United States Patent [19]

Berman et al.

[11] Patent Number: 4,857,530

[45] Date of Patent: Aug. 15, 1989

[54] SUBSTITUTED QUINAZOLINONES AS ANTICANCER AGENTS

[75] Inventors: Ellen M. Berman; Leslie M. Werbel; Dennis J. McNamara, all of Ann Arbor, Mich.

[73] Assignee: Warner-Lambert Company, Morris Plains, N.J.

[21] Appl. No.: 116,929

[22] Filed: Nov. 3, 1987

[51] Int. Cl.$^4$ .................. A61K 31/505; C07D 401/12
[52] U.S. Cl. ..................... 514/259; 514/260; 544/92; 544/284; 544/287
[58] Field of Search ............... 544/284, 287; 514/259, 514/260

[56] References Cited

FOREIGN PATENT DOCUMENTS 0239362  9/1987  European Pat. Off. .
2065653A  7/1981  United Kingdom .
2175903A  12/1986  United Kingdom .

OTHER PUBLICATIONS

Jones, et al., *Journal of Medicinal Chemistry*, vol. 29, pp. 1114–1118 (1986).

*Primary Examiner*—Glennon H. Hollrah
*Assistant Examiner*—James H. Turnipseed
*Attorney, Agent, or Firm*—Francis J. Tinney

[57] ABSTRACT

Novel 6-substituted-4(3H)-quinazolinones are described as well as methods for the preparation and pharmaceutical composition of same, which inhabit the enzyme thymidylate synthase (TS) and are thus useful as anticancer agents.

17 Claims, No Drawings

SUBSTITUTED QUINAZOLINONES AS ANTICANCER AGENTS

BACKGROUND OF THE INVENTION

The present invention relates to novel substituted quinazolinones useful as pharmaceutical agents, to methods for their production, to pharmaceutical compositions which include these compounds and a pharmaceutically acceptable carrier, and to a pharmaceutical method of treatment. More particularly, the novel compounds of the present invention inhibit the enzyme thymidylate synthase (TS) thus inhibiting the growth of malignant neoplasms in mammals.

Most traditional antifolate anticancer drugs act by inhibiting the enzyme dihydrofolate reductase (DHFR). Inhibition of DHFR has been associated clinically with the development of resistance by overproduction of DHFR. In such cases TS may become the rate limiting enzyme for continued cell growth. It has been demonstrated experimentally and clinically that inhibition of TS is a viable approach for cancer chemotherapy.

TS is the enzyme that mediates the last step in the de novo synthesis of thymidylate required for deoxyribonucleic acid (DNA). Several quinazolinone folic acid analogs have been identified as inhibitors of TS. UK Patent Application No. 2,065,653A describes a series of anti-cancer quinazoline derivatives. One analog in this series, N-(4(N-((2-amino-4-hydroxy-6-quinazolinyl)methyl)prop-2-ynylamino)benzoyl)-L-glutamic acid (CB 3717), a selective, tight binding TS inhibitor was tested in Phase I clinical trials. Minor and partial responses were reported for patients with ovarian and breast cancer. However, nondose related liver toxicity and dose limiting kidney toxicity due in part to the poor solubility of this 2-amino folate analog led to the development of second generation compounds which are devoid of this substituent. UK Patent Application No. 2,175,903A describes a related series of anti-cancer quinazolines. These 2-des amino derivatives are somewhat weaker inhibitors of TS than the 2-amino derivatives but are more selective for TS than DHFR. They are reported to retain sufficient activity to be useful anticancer agents devoid of both hepatic and renal toxicity in experimental models. European patent application 0239362 discloses additional 2-substituted quinazolines related to CB 3717.

To date, all quinazolinone inhibitors of TS were thought to require the classical glutamic acid side chain, polyglutamates thereof, or related amino acid residues for enzyme inhibitory activity and therapeutic efficacy. For example, Jones et al, *Journal of Medicinal Chemistry*, Vol. 29, pp. 1114–1118 (1986) reported that removal of the glutamate residue (formula A; R=OH) decreased TS inhibition by 84-fold over the classical antifolate analog

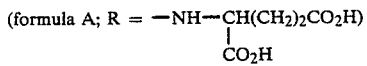

A

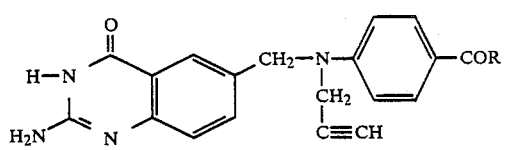

thus emphasizing the importance of an amino acid residue for strong binding to the enzyme.

Moreover, resistance to classical antifolates via impairment of the reduced folate carrier system is common and may be reasonably anticipated for the classical TS inhibitors as well. However, lipophilic antifolates, which lack the classical glutamic acid or related amino acid side chain, such as the DHFR inhibitor trimetrexate have been shown to circumvent the impaired transport seen in cells made resistant to the classical DHFR inhibitor methotrexate. Lipophilic antifolates with enzyme target other than DHFR, such as TS, might circumvent the impaired transport type of resistance often associated with classical glutamate antifolates. Therefore, we have found unexpectedly that a lipophilic non-classical series of substituted quinazolinones without the classical amino acid residue has potent selective inhibitory activity against TS.

SUMMARY OF THE INVENTION

Accordingly, the present invention relates to novel compounds having the formula I

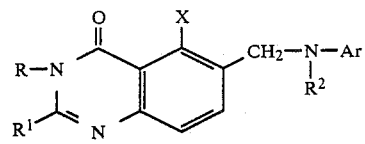

I wherein R is hydrogen, an alkyl group of one to six carbon atms, or

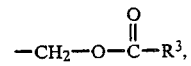

in which $R^3$ is an alkyl group of one to six carbon atoms; $R^1$ is hydrogen, an alkyl group of one to six carbon atoms, $-NR^4R^5$, in which $R^4$ and $R^5$ are each independently hydrogen or an alkyl group of one to six carbon atoms, or

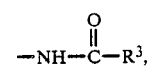

in which $R^3$ is as defined above; $R^2$ is an alkyl group of one to six carbon atoms, an alkenyl group of two to six carbon atoms, an alkynyl group of two to six carbon atoms, an alkynyl group substituted by $-NR^4R^5$, in which $R^4$ and $R^5$ are as defined above; X is hydrogen, an alkyl group of one to three carbon atoms, or halogen; Ar is

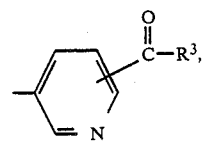

in which $R^3$ is as defined above, or

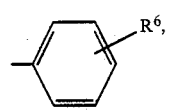

in which $R^6$ represents one or more substituents, the same or different, selected from the group consisting of hydrogen, hydroxy, alkoxy, halogen, nitro, cyano, $-OCF_3$, $-SO_2R^3$, in which $R^3$ is as defined above, $-SO_2NR^4R^5$, in which $R^4$ and $R^5$ are as defined above, $-NR^4R^5$, in which $R^4$ and $R^5$ are as defined above,

in which $R^3$ is as defined above,

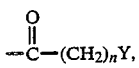

in which Y is halogen or $NR^4R^5$, in which $R^4$ and $R^5$ are as defined above and n is one to three,

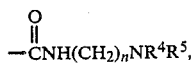

in which n, $R^4$, and $R^5$ are as defined above,

in which $R^4$ and $R^5$ are as defined above,

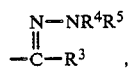

in which $R^3$, $R^4$, and $R_5$ are as defined above,

in which $R^3$ is as defined above,

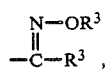

in which $R^3$ is as defined above, and

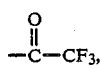

with the proviso that when $R^6$ is a single substituent $R^6$ is also selected from the group consisting of

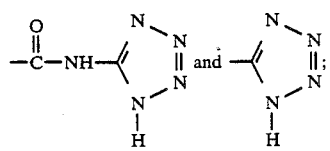

or a pharmaceutically acceptable acid or base addition salt thereof.

As inhibitors of thymidylate synthase, the compounds of formula I are useful as anticancer agents. Thus, other embodiments of the present invention include the treatment, by a compound of formula I, of malignant neoplasms in mammals.

A still further embodiment of the present invention is a pharmaceutical composition for administering an effective amount of a compound of formula I in unit dosage form in the treatment method mentioned above.

Finally, the present invention is directed to methods for production of a compound of formula I.

DETAILED DESCRIPTION OF THE INVENTION

In the compounds of formula I, the term "alkyl" means a straight or branched hydrocarbon group having from one to six carbon atoms and includes, for example, methyl, ethyl, n-propyl, isopropyl, n-butyl, isobutyl, tertiary-butyl, n-pentyl, n-hexyl, and the like.

The term "alkenyl" means a straight or branched unsaturated hydrocarbon group having from two to six carbon atoms and includes, for example, allyl, 2-butenyl, 3-methyl-3-butenyl, and the like.

The term "alkynyl" means a straight or branched triple bonded unsaturated hydrocarbon group having from two to six carbon atoms and includes, for example, 2-propynyl, 3-butynyl, 3-pentynyl, and the like.

"Alkoxy" is O-alkyl in which alkyl is as defined above.

"Halogen" is fluorine, chlorine, bromine, or iodine.

The compounds of formula I are capable of further forming both pharmaceutically acceptable acid addition and/or base salts. All of these forms are within the scope of the present invention.

In formula I, when $R^6$ is

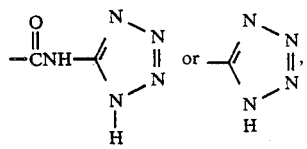

base salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine (see, for example, Berge, S. M. et al., "Pharmaceutical Salts," *Journal of Pharmaceutical Science*, 66, pp. 1–19 (1977)). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Pharmaceutically acceptable acid addition salts are formed with inorganic and organic acids, such as, for example, hydrochloric, sulfuric, phosphoric, acetic, citric, gluconic, fumaric, methanesulfonic, and the like (see, for example, Berge, S. M., et al., "Pharmaceutical Salts," *Journal of Pharmaceutical Science*, 66, pp. 1–19 (1977)). The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated as well as solvated forms, including hydrated forms. In general, the solvated forms, including hydrated forms are equivalent to unsolvated forms and are intended to be encompassed within the scope of the present invention.

A preferred compound of formula I is one wherein $R^2$ is an alkynyl group of two to six carbon atoms; or a pharmaceutically acceptable acid or base addition salt thereof.

Another preferred embodiment is a compound of formula I wherein R is hydrogen, an alkyl group of one to three carbon atoms or

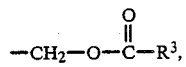

in which $R^3$ is an alkyl group of one to six carbon atoms; $R^1$ is hydrogen, $NH_2$, or

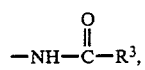

in which $R^3$ is as defined above; X is hydrogen, an alkyl group of one to three carbon atoms or halogen; AR is

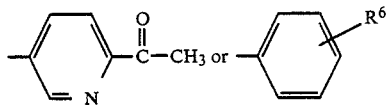

in which $R^6$ represents one or more substituents, the same or different, selected from the group consisting hydrogen, methoxy, -fluoro, -nitro, -cyano, $-OCF_3$, $-SO_2N(CH_3)_2$,

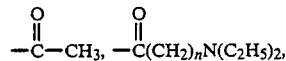

in which n is two to three,

in which n, $R^4$, and $R^5$ are as defined above,

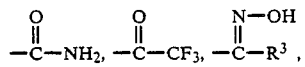

in which $R^3$ is as defined above,

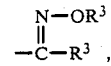

in which $R^3$ is as defined above, and

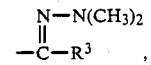

in which $R^3$ is as defined above, with the proviso that when $R^6$ is a single substituent $R^6$ is also

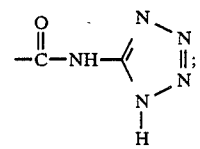

or a pharmaceutically acceptable acid or base addition salt thereof.

A further preferred embodiment is a compound of Formula I wherein AR is

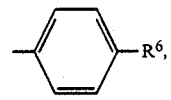

in which $R^6$ is hydrogen, hydroxy, alkoxy, halogen, nitro, cyano, $-OCF_3$, $-SO_2R^3$, in which $R^3$, is as defined above, $-SO_2NR^4R^5$, in which $R^4$ and $R^5$ are as defined above, $NR^4R^5$, in which $R^4$ and $R^5$ are as defined above,

in which $R^3$ is as defined above,

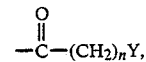

in which Y is halogen or $NR^4R^5$, in which $R^4$ and $R^5$ are as defined above and n is one to three,

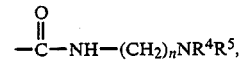

in which n, $R^4$, and $R^5$ are as defined above,

in which $R^4$ and $R^5$ are as defined above,

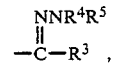

in which $R^3$, $R^4$, and $R^5$ are as defined above,

in which R³ is as defined above,

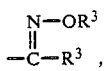

in which R³ is as defined above,

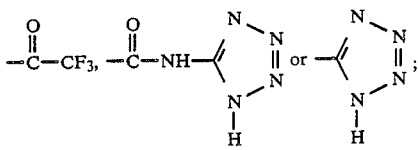

or a pharmaceutically acceptable acid or base addition salt thereof.

Particularly valuable are:

2,2-Dimethylpropanoic acid, [6-[[(4-acetylphenyl)-2-propynylamino]methyl]-4-oxo-3(4H)-quinazolinyl]methyl ester;

2,2-Dimethylpropanoic acid, [6-[[(3,4-dichlorophenyl)-2-propynylamino]methyl]-4-oxo-3(4H)-quinazolinyl]methyl ester;

2,2-Dimethylpropanoic acid, [[6-[[(2-acetyl-5-pyridinyl)-2-propynylamino]methyl]-4-oxo-3(4H)-quinazolinyl]methyl]ester;

2,2-Dimethylpropanoic acid, [4-oxo-6-[[(3,4,5-trimethoxyphenyl)-2-propynylamino]methyl]-3(4H)-quinazolinyl]methyl ester;

4-[[2-[(2,2-Dimethyl-1-oxopropyl)amino]-3,4-dihydro-4-oxo-6-quinazolinyl]methyl]-2-propynylamino]benzamide;

N-[6[[(4-Cyanophenyl)-2-propynylamino]methyl]-3,4-dihydro-4-oxo-2-quinazolinyl]-2,2-dimethylpropanamide;

N-[6-[[(4-Fluorophenyl)-2-propynylamino]methyl]-3,4-dihydro-4-oxo-2-quinazolinyl]-2,2-dimethylpropanamide;

N-[6-[[(3,4-Dichlorophenyl)-2-propynylamino]methyl]-3,4-dihydro-4-oxo-2-quinazolinyl]-2,2-dimethylpropanamide;

N-[3,4-Dihydro-4-oxo-6-[[2-propynyl[4-trifluoromethoxy)phenyl]]amino]methyl]-2-quinazolinyl]-2,2-dimethylpropanamide;

N-[3,4-Dihydro-6-[[(4-nitrophenyl)-2-propynylamino]methyl]4-oxo-2-quinazolinyl]-2,2-dimethylpropanamide;

N-[6-[[(4-Acetylphenyl)-2-propynylamino]methyl]-3,4-dihydro-4-oxo-2-quinazolinyl]-2,2-dimethylpropanamide;

N-[3,4-Dihydro-4-oxo-6-[[2-propynyl[4-(trifluoroacetyl)phenyl]amino]methyl]-2-quinazolinyl]-2,2-dimethylpropanamide;

N-[3,4-Dihydro-4-oxo-6-[[2-propynyl(3,4,5-trimethoxyphenyl)amino]methyl]-2-quinazolinyl]-2,2-dimethylpropanamide;

4-[[[2-[(2,2-Dimethyl-1-oxopropyl)amino]-3,4-dihydro-4-oxo-6-quinazolinyl]methyl]-2-propynylamino]-N-1H-tetrazol-5-ylbenzamide;

N-[6-[[[4-Dimethylamino)sulfonyl]phenyl]-2-propynylamino]methyl]-3,4-dihydro-4-oxo-2-quinazolinyl]-2,2-dimethylpropanamide;

N-[2-(Diethylamino)ethyl]-4-[[[2-dimethyl-1-oxopropyl]amino]-3,4-dihydro-4-oxo-6-quinazolinyl]methyl]-2-propynylamino]benzamide;

N-[6-[[[4-[3-(Dimethylamino)-1-oxopropyl]phenyl]-2-propynylamino]methyl]-3,4-dihydro-4-oxo-2-quinazolinyl]-2,2-dimethylpropanamide;

N-[6-[[[4-[4-(Diethylamino)-1-oxobutyl]phenyl]-2-propynylamino]methyl]-3,4-dihydro-4-oxo-2-quinazolinyl]-2,2-dimethylpropanamide;

6-[[(4-Acetylphenyl)-2-propynylamino]methyl]-4(3H)-quinazolinone;

6-[[(3,4-Dichlorophenyl)-2-propynylamino]methyl]-4(3H)-quinazolinone;

6-[[(2-Acetyl-5-pyridinyl)-2-propynylamino]methyl]-4(3H)-quinazolinone;

6-[[2-Propynyl-(3,4,5-trimethoxyphenyl)amino]methyl]-4(3H)-quinazolinone;

4-[[(2-Amino-3,4-dihydro-4-oxo-6-quinazolinyl)methyl]-2-propynylamino]benzamide;

4-[[(2-Amino-3,4-dihydro-4-oxo-6-quinazolinyl)methyl]-2-propynylamino]benzonitrile;

2-Amino-6-[[(4-fluorophenyl)-2-propynylamino]methyl]-4(3H)-quinazolinone;

2-Amino-6-[[(3,4-dichlorophenyl)-2-propynylamino]methyl]-4(3H)-quinazolinone;

2-Amino-6-[[2-propynyl[4-(trifluoromethoxy)phenyl]amino]methyl]-4-(3H)-quinazolinone;

2-Amino-6-[[(4-nitrophenyl)-2-propynylamino]methyl]-4(3H)-quinazolinone;

6-[[(4-Acetylphenyl)-2-propynylamino]methyl]-2-amino-4(3H)-quinazolinone;

2-Amino-6-[[2-propynyl[4-trifluoroacetyl)phenyl]amino]methyl]-4(3H)-quinazolinone;

2-Amino-6-[2-propynyl(3,4,5-trimethoxyphenyl)amino]methyl]-4(3H)-quinazolinone;

2-Amino-5-methyl-6-[[2-propynyl(3,4,5-trimethoxyphenyl)amino]methyl]-4(3H)-quinazolinone;

2-Amino-6-[[[4-[1-(hydroximino)ethyl]phenyl[-2-propynylamino]methyl]-4(3H)-quinazolinone;

2-Amino-6-[[[4-(1-hydrazonoethyl)phenyl]-2-propynylamino]methyl]-4(3H)-quinazolinone;

2-Amino-6-[[[4-[1-(dimethylhydrazono)ethyl]phenyl]-2-propynylamino]methyl]-4(3H)-quinazolinone;

4-[[(2-Amino-3,4-dihydro-4-oxo-6-quinazolinyl)methyl]-2-propynylamino]-N-1H-tetrazol-5-ylbenzamide;

4-[[(2-Amino-3,4-dihydro-4-oxo-6-quinazolinyl)methyl]-2-propynylamino]-N,N-dimethylbenzenesulfonamide;

4-[[(2-Amino-3,4-dihydro-4-oxo-6-quinazolinyl)methyl]-2-propynylamino]-N-[2-(diethylamino)ethyl]benzamide;

2-Amino-6-[[[4-[3-(diethylamino)-1-oxopropyl]phenyl]-2-propynylamino]methyl]-4(3H)-quinazolinone; and 2-Amino-6-[[[4-[4-(diethylamino)-1-oxobutyl]phenyl]-2-propynylamino]methyl]-4(3H)-quinazolinone; or a pharmaceutically acceptable acid or base addition salt thereof.

The compounds of formula I are valuable anticancer agents. The tests employed indicate that compounds of formula I inhibit the enzyme thymidylate synthase. Thymidylate synthase catalyzes the methylation of deoxyuridine monophosphate to thymidine monophosphate and therefore plays a key role in the synthesis of the only nucleotide required exclusively for deoxyribonucleic acid (DNA) synthesis. Inhibitors of thymidylate synthase are thus potent anitmetabolites possessing utility as antitumor agents. Thus, the compounds of formula I were tested for their ability to inhibit thymidylate synthase. Thymidylate synthase was isolated from L1210 murine leukemia cells by affinity column chromatography using the method described by Jackman, A. L., Calvert, A. H., Hart, L. I., Harrap, K. R.: Inhibition of thymidylate synthetase by the new quinazoline antifolate CB3717: enzyme purification and kinetics. In: DeBruyn, C. H. M., Simmonds, H. A., Muller, M. M. (eds.) "Purine metabolism in man, IV part B. Biochemical, immunological and cancer research." Plenum Publishing Corp., New York, 1984, pp. 375–378. Thymidylate synthase enzyme activity was determined by the tritium release assay method described by Roberts, Biochemistry, 5:3546–3548 (1966). The substrate concentrations were 50 μmolar for deoxyuridine and 100 μmolar for 5,10-methylene-tetrahydrofolate. The data in the table, expressed as $IC_{50}$ values (i.e. the concentration of compound required to inhibit 50% of the activity of thymidylate synthase), shows the activity of representative compounds of formula I.

The compounds of formula I were also tested against the L1210 murine leukemia cell line in vitro.

A cell culture of the L1210 murine leukemia cell line is grown in RPMI 1640 culture medium supplemented with 5% fetal bovine serum containing gentamicin (50 micrograms per milliliter). Dilutions of the test compound are prepared in the appropriate solvent and 20 microliters of each dilution are added to a 24-well Linbro tissue culture plate, followed by the addition of 2.0 ml of cell suspension containing $3 \times 10^4$ cells/milliliter. Solvent and medium controls are included in each test.

After incubation at 37° C. for three days in 5% $CO_2$, the contents of each well are removed and the cells are counted in a ZBI Coulter counter. The percent growth is calculated relative to the controls and the levels of drug activity are expressed as $ID_{50}$ (the concentration required to inhibit cell growth by 50%) in terms of moles/liter.

The data in the table shows the activity of representative compounds of formula I against L1210 murine leukemia cell line in vitro.

TABLE

| | Biological Activity of Compounds of Formula I | | |
|---|---|---|---|
| Example Number | Compound | $IC_{50}$ (μM) TS | $IC_{50}$ (μM) L1210 Leukemia |
| 2c | 6-[[2-Propynyl-(3,4,5-trimethoxyphenyl)amino]methyl]-4(3H)—quinazolinone. | 96 | >10 |
| 2a | 6-[[(3,4-Dichlorophenyl)-2-propynylamino]methyl]-4(3H)—quinazolinone. | 11 | 4 |
| 2 | 6-[[(4-Acetylphenyl)-2-propynylamino]methyl]-4(3H)—quinazolinone. | 2.4 | 7 |
| 2j | 6-[[(4-Acetylphenyl)-2-propynylamino]methyl]-2-amino-4(3H)—quinazolinone. | 0.77 | 4.3 |
| 2g | 2-Amino-6-[[(3,4-dichlorophenyl)-2-propynylamino]methyl]-4(3H)—quinazolinone. | 5 | 12.6 |
| 2l | 2-Amino-6-[[2-propynyl(3,4,5-trimethoxyphenyl)amino]methyl]-4(3H)—quinazolinone. | 50 | >20 |
| 2d | 4-[[2-Amino-3,4-dihydro-4-oxo-6-quinazolinyl)methy]-2-propynylamino]benzamide. | 0.64 | >20 |
| 2e | 4-[[(2-Amino-3,4-dihydro-4-oxo-6-quinazolinyl)methyl]-2-propynylamino]benzonitrile. | 1.3 | 5.9 |
| 2f | 2-Amino-6-[[(4-fluorophenyl)-2-propynylamino]methyl]-4(3H)—quinazolinone. | 11.5 | 26.1 |
| 2h | 2-Amino-6-[[2-propynyl[4-(trifluoromethoxy)phenyl]amino]methyl]-4(3H)—quinazolinone. | 11.3 | 25.1 |
| 2i | 2-Amino-6-[[(4-nitrophenyl)-2-propynylamino]methyl]-4(3H)—quinazolinone. | 0.62 | 2.4 |
| 2k | 2-Amino-6-[[2-propynyl[4-(trifluoroacetyl)phenyl]amino]methyl]-4(3H)—quinazolinone. | 0.51 | 11.8 |
| 2n | 4-[[2-Amino-3,4-dihydro-4-oxo-6-quinazolinyl)methyl]-2-propynylamino]-N,N—dimethylbenzenesulfonamide. | 1.0 | 4.1 |

The compounds of the present invention may be prepared by various methods using synthetic steps known in the literature.

Thus, for example, the compounds of formula I may be prepared according to the following Scheme I:

Scheme I

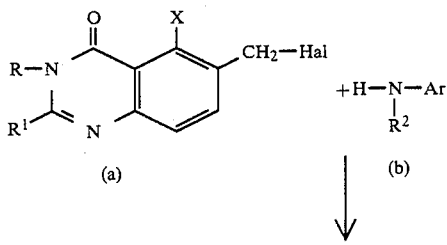

Scheme I

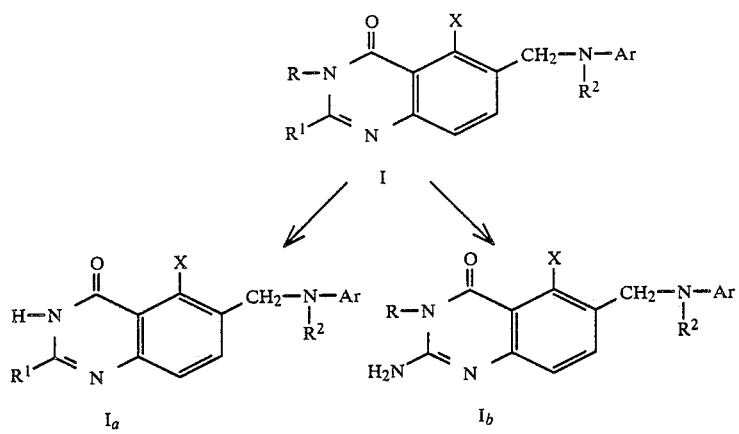

Compounds of formulas (a) and (b) in Scheme I are either known or capable of being prepared by methods known in the art.

Accordingly, reaction of a compound of formula (a) in Scheme I, in which R is hydrogen, an alkyl group of one to six carbon atoms, or

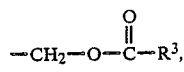

in which $R^3$ is an alkyl group of one to six carbon atoms; $R^1$ is hydrogen, an alkyl group of one to six carbon atoms, $-NR^4R^5$, in which $R^4$ and $R^5$ are each independently hydrogen or an alkyl group of one to six carbon atoms, or $$-NH-\overset{\overset{O}{\|}}{C}-R^3,$$

in which $R^3$ is as defined above; X is hydrogen, an alkyl group of one to three carbon atoms, or halogen; and Hal is a halogen, such as for example chlorine or bromine with a compound of formula (b), in which $R^2$ is an alkyl group of one to six carbon atoms, an alkenyl group of two to six carbon atoms, an alkynyl group of two to six carbon atoms, an alkynyl group substituted by $-NR^4R^5$, in which $R^4$ and $R^5$ are as defind above; Ar is

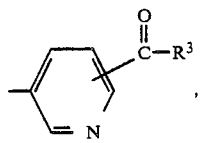

in which $R^3$ is as defined above, or

in which $R^6$ represents one or more substituents, the same or different, selected from the group consisting of hydrogen, hydroxy, alkoxy, halogen, nitro, cyano, $-OCF_3$, $-SO_2R^3$, in which $R^3$ is as defined above, $-SO_2NR^4R^5$, in which $R^4$ and $R^5$ are as defined above,
$-NR^4R^5$, in which $R^4$ and $R^5$ are as defined above, $$-\overset{\overset{O}{\|}}{C}-R^3,$$

in which $R^3$ is as defined above, $$-\overset{\overset{O}{\|}}{C}-(CH_2)_nY,$$

in which Y is halogen or $NR^4R^5$, in which $R^4$ and $R^5$ are as defined above and n is one to three, $$-\overset{\overset{O}{\|}}{C}NH(CH_2)_nNR^4R^5,$$

in which n, $R^4$, and $R^5$ are as defined above, $$-\overset{\overset{O}{\|}}{C}NR^4R^5,$$

in which $R^4$ and $R^5$ are as defined above,

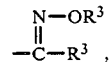

in which $R^3$, $R^4$, and $R^5$ are as defined above, $$-\overset{\overset{N-OH}{\|}}{C}-R^3,$$

in which $R^3$ is as defined above, $$-\overset{\overset{N-OR^3}{\|}}{C}-R^3,$$

in which $R^3$ is as defined above, and

with the proviso that when $R^6$ is a single substituent $R^6$ is also selected from the group consisting of

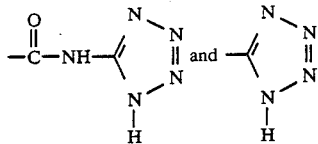

in the presence of a base and an inert solvent provides a compound of formula I wherein R, $R^1$, X, $R^2$, and Ar are as defined above. The reaction is carried out at a temperature of 25° C. to 140° C. in a suitable solvent such as acetone, toluene, acetonitrile, dimethylacetamide, and the like in the presence of a base such as pyridine, triethylamine, diisopropylethylamine, potassium carbonate, calcium carbonate, and the like. Preferably the reaction is carried out at reflux in dimethylacetamide in the presence of calcium carbonate.

Preferably, a compound of formula $I_a$, wherein $R^1$ is hydrogen, an alkyl group of one to six carbon atoms, or $NR^4R^5$, in which $R^4$ and $R^5$ are as defined above and X, $R^2$, and Ar are as defined above is prepared from a compound of formula I, wherein R is

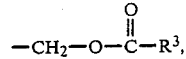

$R^1$ is hydrogen, an alkyl group of one to six carbon atoms, $NR^4R^5$, or

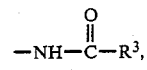

and $R^3$, $R^4$, $R^5$, $R^1$, X, $R^2$, and Ar are as defined above in the presence of a base and an inert solvent. The reaction may be carried out at a temperature of 0° C. to 25° C. in a suitable solvent such as methanol, ethanol, and the like in the presence of a base, such as triethylamine, ammonia, and the like. Preferably, the reaction is carried out at room temperature in methanol in the presence of ammonia.

Preferably, a compound of formula $I_b$, wherein R is hydrogen or an alkyl group of one to six carbon atoms and X, $R^2$, and Ar are as defined above is prepared from a compound of formula I, wherein R is hydrogen or an alkyl group of one to six carbon atoms and $R^1$ is

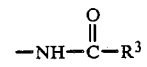

and $R^3$, X, $R^2$, and Ar are as defined above in the presence of a base and an inert solvent. The reaction may be carried out following the same procedure used to prepare a compound of formula $I_a$.

Alernatively, compounds of the present invention may be prepared according to Scheme II:

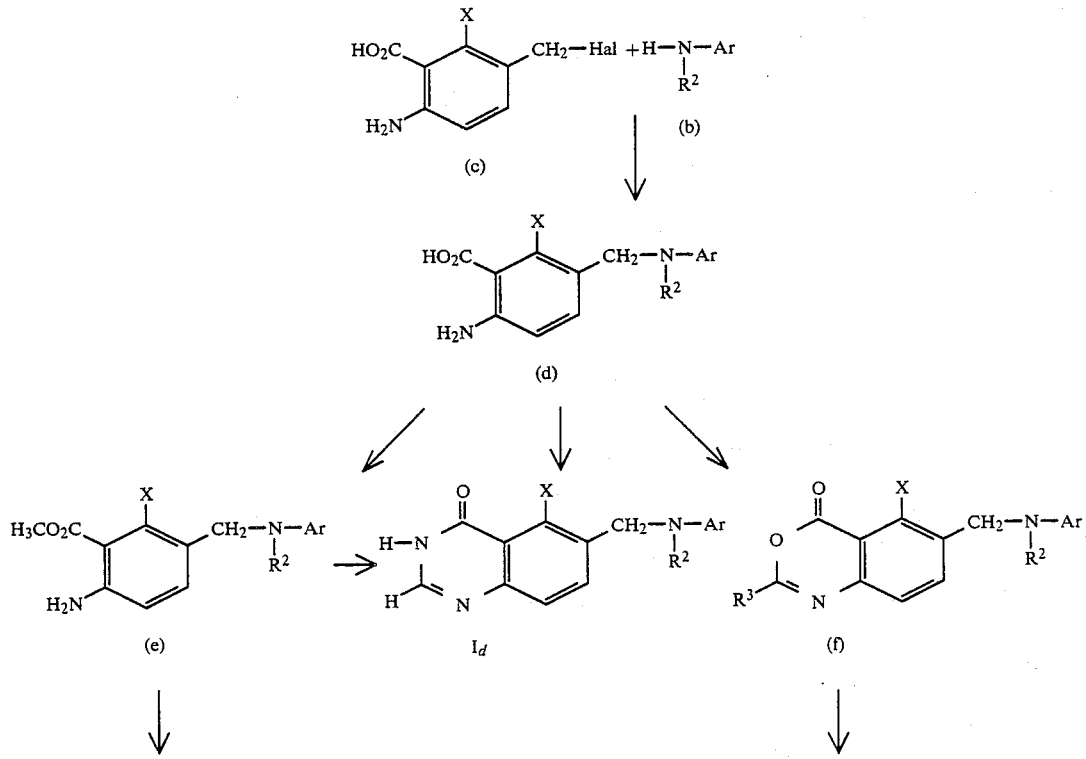

-continued
Scheme II

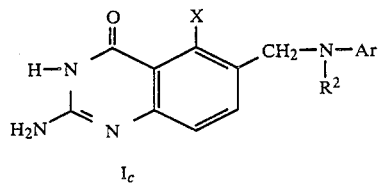

I_c

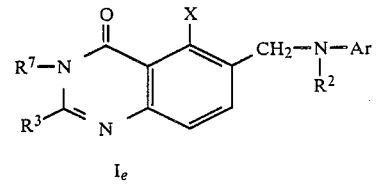

I_e

Compounds of formulas (c) and (b) in Scheme II are either known or capable of being prepared by methods known in the art.

Accordingly, reaction of a compound of formula (c) in Scheme II, in which X and Hal are as defined above with a compound of formula (b), in which $R^2$ and Ar are as defined above, in the presence of a base and an inert solvent provides a compound of formula (d) in which X, $R^2$, and Ar are as defined above. The reaction is carried out at a temperature of 25° C. to 140° C. in a suitable solvent such as acetone, toluene, acetonitrile, dimethylacetamide, dimethylformamide, and the like in the presence of a base such as pyridine, triethylamine, diisopropylethylamine, potassium carbonate, calcium carbonate, and the like.

A compound of formula (d) is esterified by standard methods known in the art to provide a methyl ester of formula (e) in which X, $R^2$, and Ar are as defined above. Reaction of a compound of formula (e), in which X, $R^2$, and Ar are as defined above with chloroformamidine, guanidine hydrochloride, guanidine carbonate, or the like in an inert solvent such as dimethylsulfone at temperatures between 25° C. and 200° C. provides a compound of formula $I_c$ wherein X, $R^2$, and Ar are as defined above.

Reaction of a compound of formula (d), in which X, $R^2$, and Ar are as defined above with formamide provides a compound of formula $I_d$ wherein X, $R^2$, and Ar are as defined above. The reaction is carried out at a temperature of 25° C. to 180° C. either without solvent or in a suitable inert solvent such as ethanol, dimethyldsulfone, and the like. Alternatively, a compound of formula $I_d$ is formed by reaction of a compound of formula (e), in which X, $R^2$, and Ar are as defined above, with formamidine acetate in a similar manner.

Reaction of a compound of formula (d), in which X, $R^2$, and Ar are as defined above, with an anhydride of formula

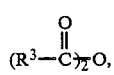

wherein $R^3$ is as defined above, such as, for example, acetic anhydride, provides 2-substituted 4H-3,1-benzoxazin-4-ones of formula (f), wherein $R^3$, X, $R^2$, and Ar are as defined above. The reaction is carried out in the anhydride alone or in a suitable inert solvent such as acetic acid at a temperature between 25° C. and 150° C. The reaction of a compound of formula (f), in which $R^3$, X, $R^2$, and Ar are as defined above, with an amine of formula $H_2N\text{-}R^7$ wherein $R^7$ is hydrogen or an alkyl group of one to six carbon atoms provides a compound of formula $I_e$, wherein $R^7$, $R^3$, X, $R^2$, and Ar are as defined above. The reaction is carried out at a temperature between 25° C. and 140° C. in a suitable inert solvent such as ethanol.

A compound of formula I may also be prepared according to Scheme III:

Scheme III

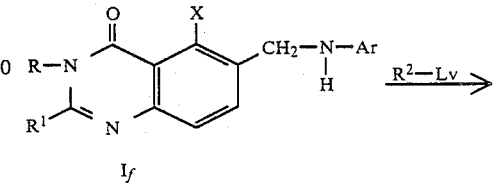

I_f

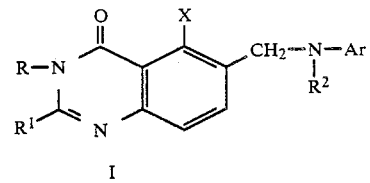

I

Thus, reaction of a compound of formula $I_f$, wherein R is hydrogen, an alkyl group of one to six carbon atoms, or

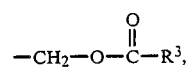

in which $R^3$ is an alkyl group of one to six carbon atoms; $R^1$ is hydrogen, an alkyl group of one to six carbon atoms, $-NR^4R^5$, in which $R^4$ and $R^5$ are each independently hydrogen or an alkyl group of one to six carbon atoms, or

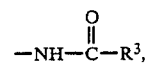

in which $R^3$ is as defined above; and X and Ar are as defined above, with an alkylating agent of formula $R^2$-Lv, wherein $R^2$ is as defined above and Lv is a leaving group such as halogen, triflate, or the like, in the presence of a base in an inert solvent provides a compound of formula I wherein R, $R^1$, X, $R^2$, and Ar are as defined above. A compound of formula $I_f$ is prepared according to Scheme I from a compound of formula (a), wherein R, $R^1$, X, and Hal are as defined above and a compound of formula (b) wherein $R^2$ is hydrogen and Ar is as defined above. The reaction may be carried out at a temperature of 25° C. to 140° C. in a suitable solvent such as acetone, ethanol, toluene, acetonitrile, dimethylacetamide, and the like in the presence of a base such as pyridine, triethylamine, diisopropylethylamine, potassium carbonate, and the like.

The compounds of the invention can be prepared and administered in a wide variety of oral and parenteral dosage forms. It will be obvious to those skilled in the art that the following dosage forms may comprise as the active component, either a compound of formula I or a corresponding pharmaceutically acceptable salt of a compound of formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active compound is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water propylene glycol solutions. For parenteral injection liquid preparations can also be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, stabilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampules. Also, the unit dosage form can be a capsule, tablet, cachet, or lozenge itself, or it can be the appropriate number of any of these in packaged form.

The quantity of active component in a unit dose preparation may be varied or adjusted from 50 mg to 1000 mg preferably 50 mg to 500 mg according to the particular application and the potency of the active component. The composition can, if desired, also contain other compatible therapeutic agents.

In therapeutic use as agents for treating tumors the compounds utilized in the pharmaceutical method of this invention are administered at the initial dosage of about 20 mg to about 1000 mg per kilogram daily. A daily dose range of about 50 mg to about 500 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

EXAMPLE 1

2,2-Dimethylpropanoic acid, [6-[[(4-acetylphenyl)-2-propynylamino]methyl]-4-oxo-3(4H)-quinazolinyl]methyl ester.

A suspension of 5.79 g (12.5 mmol) of 75% pure 2,2-dimethylpropanoic acid, [6-(bromomethyl)-4-oxo-3(4H)-quinazolinyl]methyl ester (European patent application 204,529), 2.89 g (16.7 mmol) of 1-[4-(2-propynylamino)phenyl]ethanone (see Example A), and 3.34 g (33.4 mmol) of dry calcium carbonate in 100 ml of dimethylacetamide (DMA) is stirred at 80° C. for eighteen hours. The suspension is poured into a water-ice mixture and stirred. The suspension is extracted with ethyl acetate. The ethyl acetate solution is dried (magnesium sulfate) and concentrated to give 10.4 g of a yellow oil. This is dissolved in a minimum amount of dichloromethane and applied to a column of 1 kg of flash silica gel packed in dichloromethane/methanol (100:1). Elution with the same solvent gives 2.83 g (50.8%) of impure product as a yellow gum followed by 2.34 g (42.0% assuming 75% pure bromomethyl compound) of the product as a cream colored foam. This is used as is without characterization in the next reaction.

EXAMPLE 1a 2,2-Dimethylpropanoic acid, [6-[[(3,4-dichlorophenyl)-2-propynylamino]methyl]-4-oxo-3(4H)-quinazolinyl]methyl ester.

In a process analogous to Example 1 by substituting 3,4-dichloro-N-2-propynylbenzenamine (see Example B) for 1-[4-(2-propynylamino)phenyl]ethanone one obtains 2,2-dimethylpropanoic acid, [6-[[(3,4-dichlorophenyl)-2-propynylamino]methyl]-4-oxo-3(4H)-quinazolinyl]methyl ester, as a clear colorless oil.

EXAMPLE 1b 2,2-Dimethylpropanoic acid, [[6-[[(2-acetyl-5-pyridinyl)-2-propynylamino]methyl]-4-oxo-3(4H)-quinazolinyl]ester.

In a process analogous to Example 1 by substituting 1-[5-(2-propynylamino)-2-pyridinyl]ethanone (see Example C) for 1-[4-(2-propynylamino)phenyl]ethanone one obtains 2,2-dimethylpropanoic acid, [6-[[(2-acetyl-5-pyridinyl)-2-propynylamino]methyl]-4-oxo-3(4H)-quinazolinyl]methyl ester.

EXAMPLE 1c 2,2-Dimethylpropanoic acid, [4-oxo-6-[[(3,4,5-trimethoxyphenyl)-2-propynylamino]-methyl]-3(4H)-quinazolinyl]methyl ester.

In a process analogous to Example 1 by substituting 3,4,5-trimethoxy-N-2-propynylbenzenamine (see Example D) for 1-[4-(2-propynylamino)phenyl]ethanone one obtains 2,2-dimethylpropanoic acid, [4-oxo-6[[(3,4,5-trimethoxyphenyl)-2-propynylamino]methyl]-3(4H)-quinazolinyl]methyl ester as a light brown oil.

EXAMPLE 1d

4-[[[2-[(2,2-Dimethyl-1-oxopropyl)amino]-3,4-dihydro-4-oxo-6-quinazolinyl]methyl]-2-propynylamino]benzamide.

In a process analogous to Example 1 by substituting 4-(2-propynylamino)benzamide (see Example E) for 1-[4-(2-propynylamino)phenyl]ethanone and N-[6-(bromomethyl)-3,4-dihydro-4-oxo-2-quinazolinyl]-2,2-dimethylpropanamide (*Journal of Heterocyclic Chemistry*, Vol. 12, pp. 1283–1286 (1975)) for 2,2-dimethylpropanoic acid, [6-(bromomethyl)-4-oxo-3(4H)-quinazolinyl]methyl ester (European patent application 204,529) one obtains 4-[[[2-[(2,2-dimethyl-1-oxopropyl)amino]-3,4-dihydro-4-oxo-6-quinazolinyl]methyl]-2-propynylamino]benzamide; mp 147°–153° C.

EXAMPLE 1e

4-[[[2-[(2,2-Dimethyl-1-oxopropyl)amino]-3,4-dihydro-4-oxo-6-quinazolinyl]methyl]-2-propynylamino]benzonitrile In a process analogous to Example 1 by substituting 4-(2-propynylamino)benzonitrile (see Example F) for 1-[4-(2-propynylamino)phenyl]ethanone and N-[6-(bromomethyl)-3,4-dihydro-4-oxo-2-quinazolinyl]-2,2-dimethylpropanamide (*Journal of Heterocyclic Chemistry*, Vol. 12, pp. 1283–1286 (1975)) for 2,2-dimethylpropanoic acid, [6-(bromomethyl)-4-oxo-3(4H)-quinazolinyl]methyl ester (European patent application No. 204,529) one obtains 4-[[[2-[(2,2-dimethyl-1-oxopropyl)amino]-3,4-dihydro-4-oxo-6-quinazolinyl]methyl]-2-propynylamino]benzonitrile; mp 183°–186° C.

EXAMPLE 1f

N-[6-[[(4-Fluorophenyl)-2-propynylamino]methyl]-3,4-dihydro-4-oxo-2-quinazolinyl]-2,2-dimethylpropanamide In a process analogous to Example 1 by substituting 4-fluoro-N-2-propynylbenzenamine (see Example G) for 1-[4-(2-propynylamino)phenyl]ethanone and N-[6-(bromomethyl)-3,4-dihydro-4-oxo-2-quinazolinyl]-2,2-dimethylpropanamide (*Journal of Heterocyclic Chemistry*, Vol. 12, pp. 1283–1286 (1975)) for 2,2-dimethylpropanoic acid, [6-(bromomethyl)-4-oxo-3(4H)-quinazolinyl]methyl ester (European patent application No. 204,529) one obtains N-[6-[[(4-fluorophenyl)-2-propynylamino]methyl]-3,4-dihydro-4-oxo-2-quinazolinyl]-2,2-dimethylpropanamide; mp 187°–190° C.

EXAMPLE 1g

N-[6-[[(3,4-Dichlorophenyl)-2-propynylamino]methyl]-3,4-dihydro-4-oxo-2-quinazolinyl]-2,2-dimethylpropanamide In a process analogous to Example 1 by substituting 3,4-dichloro-N-2-propynylbenzenamine (see Example B) for 1-[4-(2-propynylamino)phenyl]ethanone and N-[6-(bromomethyl)-3,4-dihydro-4-oxo-2-quinazolinyl]-2,2-dimethylpropanamide (*Journal of Heterocyclic Chemistry*, Vol. 12, pp. 1283–1286 (1975)) for 2,2-dimethylpropanoic acid, [6-(bromomethyl)-4-oxo-3(4H)-quinazolinyl]methyl ester (European patent application No. 204,529) one obtains N-[6-[[(3,4-dichlorophenyl)-2-propynylamino]methyl-3,4-dihydro-4-oxo-2-quinazolinyl]-2,2-dimethylpropanamide as an off-white solid.

EXAMPLE 1h

N-[3,4-Dihydro-4-oxo-6-[[2-propynyl[4-(trifluoromethoxy)phenyl]amino]methyl]-2-quinazolinyl]-2,2-dimethylpropanamide In a process analogous to Example 1 by substituting N-2-propynyl-4-(trifluoromethoxy)benzenamine (see Example H) for 1-[4-(2-propynylamino)phenyl]ethanone and N-[6-(bromomethyl)-3,4-dihydro-4-oxo-2-quinazolinyl]-2,2-dimethylpropanamide (*Journal of Heterocyclic Chemistry*, Vol. 12, pp. 1283–1286 (1975)) for 2,2-dimethylpropanoic acid, [6-(bromomethyl)-4-oxo-3(4H)-quinazolinyl]methyl ester (European patent application No. 204,529) one obtains N-[3,4-dihydro-4-oxo-6-[[2-propynyl[4-(trifluoromethoxy)phenyl]amino]methyl]-2-quinazolinyl]-2,2-dimethylpropanamide; mp 174°–176° C.

EXAMPLE 1i

N-[3,4-Dihydro-6-[[(4-nitrophenyl)-2-propynylamino]methyl]-4-oxo-2-quinazolinyl]-2,2-dimethylpropanamide In a process analogous to Example 1 by substituting 4-nitro-N-2-propynylbenzenamine (see Example I) for 1-[4-(2-propynylamino)phenyl]ethanone and N-[6-(bromomethyl)-3,4-dihydro-4-oxo-2-quinazolinyl]-2,2-dimethylpropanamide (*Journal of Heterocyclic Chemistry*, Vol. 12, pp. 1283–1286 (1975)) for 2,2-dimethylpropanoic acid, [6-(bromomethyl)-4-oxo-3(4H)-quinazolinyl]methyl ester (European patent application No. 204,529) one obtains N-[3,4-dihydro-6-[[(4-nitrophenyl)-2-propynylamino]methyl]-4-oxo-2-quinazolinyl]-2,2-dimethylpropanamide; mp 210°–215° C.

EXAMPLE 1j

N-[6-[[(4-Acetylphenyl)-2-propynylamino]methyl]-3,4-dihydro-4-oxo-2-quinazolinyl]-2,2-dimethylpropanamide In a process analogous to Example 1 by substituting N-[6-(bromomethyl)-3,4-dihydro-4-oxo-2-quinazolinyl]-2,2-dimethylpropanamide (*Journal of Het-

EXAMPLE 1k

N-[3,4-Dihydro-4-oxo-6-[[2-propynyl[4-(trifluoroacetyl)phenyl]amino]methyl]-2-quinazolinyl]-2,2-dimethylpropanamide In a process analogous to Example 1 by substituting 2,2,2-trifluoro-1-[4-(2-propynylamino)phenyl]ethanone (see Example J) for 1-[4-(2-propynylamino)phenyl]ethanone and N-[6-(bromomethyl)-3,4-dihydro-4-oxo-2-quinazolinyl]-2,2-dimethylpropanamide (*Journal of Heterocyclic Chemistry*, Vol. 12, pp. 1283–1286 (1976)) for 2,2-dimethylpropanoic acid, [6-(bromomethyl)-4-oxo-3(4H)-quinazolinyl]methyl ester (European patent application No. 204,529) one obtains N-[3,4-dihydro-4-oxo-6-[[2-propynyl[(4-trifluoroacetyl)phenyl]amino]methyl]-2-quinazolinyl]-2,2-dimethylpropanamide as a cream colored foam.

EXAMPLE 1l

N-[3,4-Dihydro-4-oxo-6-[[2-propynyl(3,4,5-trimethoxyphenyl)amino]methyl]-2-quinazolinyl]-2,2-dimethylpropanamide In a process analogous to Example 1 by substituting 3,4,5-trimethoxy-N-2-propynylbenzenamine (see Example D) for 1-[4-(2-propynylamino)phenyl]ethanone and N-[6-(bromomethyl)-3,4-dihydro-4-oxo-2-quinazolinyl]-2,2-dimethylpropanamide (*Journal of Heterocyclic Chemistry*, Vol. 12, pp. 1283–1286 (1975)) for 2,2-dimethylpropanoic acid, [6-(bromomethyl)-4-oxo-3(4H)-quinazolinyl]methyl ester (European patent application No. 204,529) one obtains N-[3,4-dihydro-4-oxo-6-[[2-propynyl(3,4,5-trimethoxyphenyl)amino]methyl]-2-quinazolinyl]-2,2-dimethylpropanamide.

EXAMPLE 1m

4-[[[2-[(2,2-Dimethyl-1-oxopropyl)amino]-3,4-dihydro-4-oxo-6-quinazolinyl]methyl]-2-propynylamino]-N-1H-tetrazol-5-ylbenzamide In a process analogous to Example 1 by substituting 4-(2-propynylamino)-N-1H-tetrazol-5-ylbenzamide (see Example K) for 1-[4-(2-propynylamino)phenyl]ethanone and N-[6-(bromomethyl)-3,4-dihydro-4-oxo-2-quinazolinyl]-2,2-dimethylpropanamide (*Journal of Heterocyclic Chemistry*, Vol. 12, pp. 1283–1286 (1975)) for 2,2-dimethylpropanoic acid, [6-(bromomethyl)-4-oxo-3(4H)-quinazolinyl]methyl ester (European patent application No. 204,529) one obtains 4-[[[2-[(2,2-dimethyl-1-oxopropyl)amino]-3,4-dihydro-4-oxo-6-quinazolinyl]methyl]-2-propynylamino]-N-1H-tetrazol-5-ylbenzamide.

EXAMPLE 1n

N-[6-[[[4-[(Dimethylamino)sulfonyl]phenyl]-2-propynylamino]methyl]-3,4-dihydro-4-oxo-2-quinazolinyl]-2,2-dimethylpropanamide In a process analogous to Example 1 by substituting N,N-dimethyl-4-(2-propynylamino)benzenesulfonamide (see Example L) for 1-[4-(2-propynylamino)phenyl]ethanone and N-[6-(bromomethyl)-3,4-dihydro-4-oxo-2-quinazolinyl]-2,2-dimethylpropanamide (*Journal of Heterocyclic Chemistry*, Vol. 12, pp. 1283–1286 (1975)) for 2,2-dimethylpropanoic acid, [6-(bromomethyl)-4-oxo-3(4H)-quinazolinyl]methyl ester (European patent application No. 204,529) one obtains N-[6-[[[4-[(dimethylamino)sulfonyl]phenyl]-2-propynylamino]methyl]-3,4-dihydro-4-oxo-2-quinazolinyl]-2,2-dimethylpropanamide; mp 217°–220° C.

EXAMPLE 1o

N-[2-(Diethylamino)ethyl]-4-[[[2-[(2,2-dimethyl-1-oxopropyl)amino]-3,4-dihydro-4-oxo-6-quinazolinyl]methyl]-2-propynylamino]benzamide In a process analogous to Example 1 by substituting N-[2-(diethylamino)ethyl]-4-(2-propynylamino)benzamide (see Example M) for 1-[4-(2-propynylamino)phenyl]ethanone and N-[6-(bromomethyl)-3,4-dihydro-4-oxo-2-quinazolinyl]-2,2-dimethylpropanamide (*Journal of Heterocyclic Chemistry*, Vol. 12, pp. 1283–1286 (1975)) for 2,2-dimethylpropanoic acid, [6-(bromomethyl)-4-oxo-3(4H)-quinazolinyl]methyl ester (European patent application No. 204,529) one obtains N-[2-(diethylamino)ethyl]-4-[[[2-[(2,2-dimethyl-1-oxopropyl)amino]-3,4-dihydro-4-oxo-6-quinazolinyl]methyl]-2-propynylamino]benzamide.

EXAMPLE 1p

N-[6-[[[4-[3-(Diethylamino)-1-oxopropyl]phenyl]-2-propynylamino]methyl]-3,4-dihydro-4-oxo-2-quinazolinyl]-2,2-dimethylpropanamide In a process analogous to Example 1 by substituting 3-(diethylamino)-1-[4-(2-propynylamino)phenyl]-1-propanone (see Example N) for 1-[4-(2-propynylamino)phenyl]ethanone and N-[6-(bromomethyl)-3,4-dihydro-4-oxo-2-quinazolinyl]-2,2-dimethylpropanamide (*Journal of Heterocyclic Chemistry*, Vol. 12, pp. 1283–1286 (1975)) for 2,2-dimethylpropanoic acid, [6-(bromomethyl)-4-oxo-3(4H)-quinazolinyl]methyl ester (European patent application No. 204,529) one obtains N-[6-[[[4-[3-(diethylamino)-1-oxopropyl]phenyl]-2-propynylamino]methyl]-3,4-dihydro-4-oxo-2-quinazolinyl]-2,2-dimethylpropanamide.

EXAMPLE 1q

N-[6-[[[4-[4-(Diethylamino)-1-oxobutyl]phenyl]-2-propynylamino]methyl]-3,4-dihydro-4-oxo-2-quiazolinyl]-2,2-dimethylpropanamide In a process analogous to Example 1 by substituting 4-(diethylamino)-1-[4-(2-propynylamino)phenyl]-1-butanone (see Example O) for 1-[4-(2-propynylamino)phenyl]ethanone and N-[6-(bromomethyl)-3,4-dihydro-4-oxo-2-quinazolinyl]-2,2-dimethylpropanamide (*Journal of Heterocyclic Chemistry*, Vol. 12, pp. 1283–1286 (1975)) for 2,2-dimethylpropanoic acid, [6-(bromomethyl)-4-oxo-3(4H)-quinazolinyl]methyl ester (European patent application No. 204,529) one obtains N-[6-[[[4-[4-(diethylamino)-1-oxobutyl]phenyl]-2-propynylamino]methyl]-3,4-dihydro-4-oxo-2-quinazolinyl]-2,2-dimethylpropanamide.

EXAMPLE 2

6-[[(4-Acetylphenyl)-2-propynylamino]methyl]-4(3H)-quinazolinone

To 2.34 g (5.25 mmol) of 2,2-dimethylpropanoic acid, [6-[[(4-acetylphenyl)-2-propynylamino]methyl]-4-oxo-3(4H)-quinazolinyl]methyl ester (Example 1) is added a solution of 500 ml of methanol saturated with ammonia at 20° C. The solution is stirred at room temperature for eighteen hours. The solution is concentrated to give a solid which is recrystallized from ethanol to give the product as a pink solid; mp 197°–199° C.

In a process analogous to Example 2 using appropriate starting materials the corresponding compounds of formula I are prepared as follows:

EXAMPLE 2a

6-[[(3,4-Dichlorophenyl)-2-propynylamino]methyl]-4(3H)-quinazolinone; mp 211°–213° C.

EXAMPLE 2b

6-[[(2-Acetyl-5-pyridinyl)-2-propynylamino]methyl]-4(3H)-quinazolinone.

EXAMPLE 2c

6-[[2-Propynyl-(3,4,5-trimethoxyphenyl)amino]methyl]-4(3H)-quinazolinone; mp 167°–169° C.

EXAMPLE 2d

4-[[(2-Amino-3,4-dihydro-4-oxo-6-quinazolinyl)methyl]-2-propynylamino]benzamide, containing 0.3 mole of water; mp >275° C.

EXAMPLE 2e

4-[[(2-Amino-3,4-dihydro-4-oxo-6-quinazolinyl)methyl]-2-propynylamino]benzonitrile, containing one-half mole of water; mp 251°–253° C.

EXAMPLE 2f

2-Amino-6-[[(4-fluorophenyl)-2-propynylamino]methyl]-4(3H)-quinazolinone; mp 251°–252° C.

EXAMPLE 2g

2-Amino-6-[[(3,4-Dichlorophenyl)-2-propynylamino]methyl]-4(3H)-quinazolinone; mp 251°–253° C.

EXAMPLE 2h

2-Amino-6-[[2-propynyl[4-(trifluoromethoxy)phenyl]amino]methyl]-4(3H)-quinazolinone; mp 247°–249° C.

EXAMPLE 2i

2-Amino-6-[[(4-nitrophenyl)-2-propynylamino]methyl]-4(3H)-quinazolinone, containing one-quarter mole of water; mp 254°–259° C.

EXAMPLE 2j

6-[[(4-Acetylphenyl)-2-propynylamino]methyl]-2-amino-4(3H)-quinazolinone; mp 255°–258° C.

EXAMPLE 2k

2-Amino-6-[[2-propynyl[4-(trifluoroacetyl)phenyl]amino]methyl]-4(3H)-quinazolinone, containing 0.3 mole of water; mp 231°–234° C.

EXAMPLE 2l

2-Amino-6-[[2-propynyl(3,4,5-trimethoxyphenyl)amino]methyl]-4(3H)-quinazolinone, containing 0.3 mole of water; mp 236°–238° C.

EXAMPLE 2m

4-[[(2-Amino-3,4-dihydro-4-oxo-6-quinazolinyl)methyl]-2-propynylamino]-N-1H-tetrazol-5-ylbenzamide.

EXAMPLE 2n

4-[[(2-Amino-3,4-dihydro-4-oxo-6-quinazolinyl)methyl]-2-propynylamino]-N,N-dimethylbenzenesulfonamide, containing 1.7 mole of water; mp 247°–250° C. (dec).

EXAMPLE 2o

4-[[(2-Amino-3,4-dihydro-4-oxo-6-quinazolinyl)methyl]-2-propynylamino]-N-[2-(diethylamino)ethyl]benzamide.

EXAMPLE 2p

2-Amino-6-[[[4-[3-(diethylamino)-1-oxopropyl]phenyl]-2-propynylamino]methyl]-4(3H)-quinazolinone.

EXAMPLE 2q

2-Amino-6-[[[4-[4-(diethylamino)-1-oxobutyl]phenyl]-2-propynylamino]methyl]-4(3H)-quinazolinone.

EXAMPLE 3

2-Amino-5-methyl-6-[[2-propynyl(3,4,5-trimethoxyphenyl)amino]methyl]-4(3H)-quinazolinone A suspension of 0.10 g (0.27 mmol) of 2-amino-5-methyl-6-[[(3,4,5-trimethoxyphenyl)amino]methyl]-4(3H)-quinazolinone, (see Example P) 0.54 ml (2.7 mmol) of an 80% solution of 3-bromo-1-propyne in toluene, and 0.42 ml (3.0 mmol) of triethylamine in 10 ml of ethanol is heated under reflux for eighteen hours. The solution is cooled, concentrated, and combined with material obtained from a similar experiment also using 0.10 g of starting material. The residue is dissolved in methanol and treated with 10 g of flash silica gel. The methanol is evaporated and the powder is applied to a column of 100 g of flash silica gel packed in dichloromethane/methanol (50:1). Elution with the same solvent initially, gradually increasing the polarity to dichloromethane/methanol (10:1) gives 0.07 g of a glassy material. Two recrystallizations from ethanol gives 0.0196 g (8.5%) of the product as an off-white solid, mp 202°–204° C.

EXAMPLE 4

2-Amino-6-[[[4-[1-(dimethylhydrazono)ethyl]phenyl]-2-propynylamino]methyl]-4(3H)-quinazolinone A suspension of 3.46 g (10 mmol) of 6-[[(4-acetylphenyl)-2-propynylamino]methyl]-2-amino-4(3H)-quinazolinone (see Example 2j) and 6.01 g (100 mmol) of 1,1-dimethylhydrazine in 250 ml of methanol is heated under reflux for eighteen hours. The solution is concentrated and the residue recrystallized from methanol to give the product.

PREPARATIVE EXAMPLES FOR INTERMEDIATES

Example A

1-[4-(2-Propynylamino)phenyl]ethanone

A mixture of 25 g (0.185 mol) of 4-aminoacetophenone, 12.7 ml (0.176 mol) of propargyl chloride, and 35 ml of diisopropylethylamine in 500 ml of dry toluene is stirred at 60° C. for eight hours then at 90° C. for twenty-four hours. The reaction is cooled to room temperature and poured into a saturated sodium bicarbonate solution. The organic portion is separated and concentrated in vacuo to an orange oil. The oil is chromatographed on silica gel eluting with a gradient of 20–50% ethyl acetate in hexane. The appropriate fractions are concentrated to leave a pale yellow solid. The solid is recrystallized from ethanol to give two crops of the desired product, 14.99 g (49% yield); mp 97°–100° C.

Example B

3,4-Dichloro-N-2-propynylbenzenamine

A solution of 16.20 g (0.1 mol) of 3,4-dichlorobenzenamine, 16.36 g (0.11 mol) of an 80% solution of 3-bromo-1-propyne in toluene, and 17.4 ml (0.11 mol) of N-ethyl-N-(1-methylethyl)-2-propanamine in 350 ml of toluene is heated at 90° for six hours. Ethyl acetate is added to the reaction suspension, and the suspension is washed three times with water. The organic layer is separated, dried (magnesium sulfate), and concentrated to give 19.85 g of a dark brown liquid. This is applied to a column of 1 kg of flash silica gel packed in hexane/dichloromethane (5:1). Elution with the same solvent gives 1.48 g (11.3%) of 3,4-dichloro-N,N-di-2-propynylbenzenamine as a yellow oil which crystallizes on standing; mp 48°–50° C. Further elution gives 15.80 g (79%) of the desired product as a gold liquid. NMR (200 MHz, DMSO) $\delta$=3.13 (t, J<3 Hz, 1, C≡CH), 3.92 (d, J<3 Hz, 2, CH$_2$), 6.48 (br s, 1, NH, disappears on D$_2$O addition), 6.64 (dd, J=8.9 Hz, 2.8 Hz, 1, 6H), 6.84 (d, J<3 Hz, 1, 2H), 7.32 (d, J=8.9 Hz, 1, 5H); MS (DEI): m/e=199 (M+); IR (LF): =3297, 1601, 1494 cm$^{-1}$.

Example C

1-[5-(2-Propynylamino)-2-pyridinyl]ethanone

2-Acetyl-5-aminopyridine, (*Journal of Heterocyclic Chemistry*, Vol. 10, pp. 1047–1049 (1973)), 25 g (0.161 mol), is dissolved in 600 ml of dry acetone. To this solution is added an 80% solution of propargyl bromide in toluene, 32 ml, and finely powdered potassium carbonate, 27 g. The solution is heated under reflux for thirty-six hours and then allowed to cool to room temperature. The reaction mixture is concentrated in vacuo and the residue is partitioned between dichloromethane and water. The organic portion is separated and the water layer extracted several times with dichloromethane. The combined organics are concentrated in vacuo to a semi-solid residue consisting of a mixture of starting material and a small amount of the monoalkylated product. The residue is triturated with a mixture of toluene and diethyl ether. The solid is removed by filtration and the filtrate is concentrated to an oil. Chromatography of the oil on silica gel with dichloromethane gives the desired product.

Example D

3,4,5-Trimethoxy-N-2-propynylbenzenamine

A solution of trimethoxyaniline, 25 g (0.137 mol), in 550 ml of toluene is heated at 90° C. with an 80% solution of propargyl bromide in toluene, 17 ml, and diisopropylethyl amine, 26 ml, for four hours. The reaction is allowed to cool to room temperature before being diluted with ethyl acetate. The solution is washed several times with a saturated solution of sodium bicarbonate and the organic portion is separated, dried, filtered, and concentrated to a dark orange oil.

The residue is dissolved in 150 ml of toluene. The solution is filtered to remove a small amount of solid and concentrated to a small volume. This is applied to a column of 1 kg of flash silica gel packed in toluene-ethyl acetate (5:1). Elution with the same solvent gives 5.55 g (16%) of 3,4,5-trimethoxy-N,N-di-2-propynylbenzenamine as a yellow oil which crystallizes on standing; mp 71°–73° C. Further elution gives 25.01 g (82.5%) of the desired product as a gold oil which crystallizes on standing; mp 62°–63° C.

Example E

4-(2-Propynylamino)benzamide

A suspension of 13.62 g (0.1 mol) of 4-aminobenzamide, 17.85 g (0.12 mol) of an 80% solution of 3-bromo-1-propyne in toluene, and 13.98 ml (0.12 mol) of 2,6-dimethylpyridine in 140 ml of dimethylacetamide (DMA) is stirred at 60° C. for two hours and then at 90° C. for one hour. The solution is cooled and the precipitated solid is collected and discarded. The filtrate is poured into a water-ice mixture and stirred. The suspension is extracted with ethyl acetate. The ethyl acetate solution is separated, dried (magnesium sulfate), and concentrated to give 20.7 g of a brown liquid. This is applied to a column of 1 kg of flash silica gel packed in dichloromethane-methanol (50:1). Elution with the same solvent gives 6.73 g (38.7%) of the product as a yellow solid, mp 139°–141° C.

Example F

4-(2-Propynylamino)benzonitrile

A suspension of 23.63 g (0.2 mol) of 4-aminobenzonitrile, 32.72 g (0.22 mol) of an 80% solution of 3-bromo-1-propyne in toluene, and 38.3 ml (0.22 mol) of N-ethyl-N-(1-methylethyl)-2-propanamine in 500 ml toluene is heated at 90° C. for eighteen hours. Ethyl acetate is added to the reaction suspension, and the suspension is washed three times with water. The organic layer is separated, dried (magnesium sulfate), and concentrated to give 32.5 g of a dark brown oil which crystallizes on standing. This is dissolved in a minimum amount of toluene and applied to a column of 1 kg of flash silica gel which is packed in toluene-ethyl acetate (20:1). Elution with the same solvent gives 24.66 g (78.9%) of the product as a cream colored solid; mp 68°–70° C.

Example G

4-Fluoro-N-2-propynylbenzenamine

A solution of 9.47 ml (0.1 mol) of 4-fluorobenzenamine, 16.36 g (0.11 mol) of an 80% solution of 3-bromo-1-propyne in toluene, and 17.43 ml (0.11 mol) of N-ethyl-N-(1-methylethyl)-2-propanamine in 350 ml of toluene is heated at 90° C. for three hours. Ethyl acetate is added to the reaction suspension, and it is washed three times with water. The organic layer is separated, dried (magnesium sulfate), and concentrated to give 15.5 g of a dark brown liquid. This is applied to a column of 1 kg of flash silica gel packed in heptane-dichloromethane (5:1). Elution with the same solvent gives 9.09 g (61%) of the product as a yellow oil.

Example H

N-2-Propynyl-4-(trifluoromethoxy)benzenamine

A solution of 8.86 g (50 mmol) of 4-(trifluoromethoxy)benzenamine, 8.18 g (55 mmol) of an 80% solution of 3-bromo-1-propyne in toluene, and 8.72 ml (50 mmol) of N-ethyl-N-(1-methylethyl)-2-propanamine in 200 ml of toluene is heated at 90° C. for eighteen hours. The suspension is cooled and treated with ethyl acetate. The suspension is washed several times with water. The ethyl acetate layer is separated, dried (magnesium sulfate), and concentrated to give a brown liquid. This is applied to a column of 1 kg of flash silica gel packed in n-heptane-dichloromethane (2:1). Elution with the same solvent gives 7.12 g (66.2%) of the product as a brown liquid.

Example I

4-Nitro-N-2-propynylbenzenamine

A mixture of 26.6 g (189 mmol) of 4-fluoronitrobenzene, 20.8 g (377 mmol) of propargylamine, 11 g (189 mmol) of potassium fluoride, and 26 g (188 mmol) of potassium carbonate in 600 ml of dimethylsulfoxide is stirred at room temperature under a nitrogen atmosphere for twenty hours. The reaction mixture is poured into 1.5 l of water and stirred at room temperature for two hours. The yellow solid is filtered, rinsed with water, and then isopropyl alcohol. The product is dried in vacuo at 50° C. for two days to give 16.27 g (49%) 4-nitro-N-2-propynylbenzenamine; mp 150°–153° C.

Example J 2,2,2-Trifluoro-1-[4-(2-propynylamino)phenyl]ethanone

To a solution of 8.64 g (45 mmol) of 2,2,2-trifluoro-1-(4-fluorophenyl)ethanone (*Journal of Organic Chemistry*, Vol. 32, pp. 1311–1318 (1967)) and 7.53 ml (54 mmol) of triethylamine in 150 ml of acetonitrile, cooled in an ice-bath, is added 31.13 ml (0.45 mol) of 2-propynylamine. The ice-bath is removed and the solution is heated under reflux for eighteen hours. The reaction solution is cooled and concentrated to give a solid, which is partitioned between ethyl acetate and water. The ethyl acetate layer is separated, dried (magnesium sulfate), and concentrated to give 10.23 g of a red-brown oil. This is applied to a column of 250 g of flash silica gel packed in n-heptane-dichloromethane (2:1). Elution with the same solvent gives 4.05 g (39.6%) of the product as a fluffy white solid; mp 96°–98° C.

Example K 4-(2-Propynylamino)-N-1H-tetrazol-5-yl-benzamide

A cold solution of 5 g (0.036 mol) of 4-fluorobenzoic acid in 150 ml of dimethylacetamide is treated dropwise with 2.9 ml (4.71 g, 0.0396 mol) of thionyl chloride and allowed to warm to room temperature over twelve hours. Anhydrous 5-aminotetrazole, 6.7 g (0.0792 mol), is added and the reaction is heated at 100° C. for fifteen hours. The reaction is permitted to cool to room temperature before being poured into water. The precipitate is collected, washed with water, dried, and recrystallized from ethanol to give 7.1 g (96%) of 4-N-N-1H-tetrazol-5-ylbenzamide; mp 293°–294° C.

A mixture of 20 g (0.097 mol) of 4-fluoro-N-1H-tetrazol-5-ylbenzamide, 12.8 ml (0.193 mol) of propargylamine, 5.6 g of anhydrous potassium fluoride, and 13 g of potassium carbonate, in 320 ml of dimethylsulfoxide is heated at 50°–70° C. for six to twenty hours. The reaction is poured into water and the precipitate is collected, washed with water, and dried in vacuo to give the title compound.

Example L

N,N-Dimethyl-4-(2-propynylamino)benzenesulfonamide

Under an atmosphere of nitrogen gas, a mixture of 17 g (0.0085 mol) of 4-amino-N,N-dimethylbenzenesulfonamide, 25.5 ml (0.229 mol) of propargyl bromide, and 20.4 ml (0.175 mol) of 2,6-lutidine in 250 ml of N,N-dimethylacetamide is stirred at 90° for three and one-half hours, allowed to cool, and concentrated in vacuo. The concentrate is taken up in dichloromethane and water; the organic layer is separated, washed with brine, dried (magnesium sulfate), filtered, and concentrated in vacuo. The residue is chromatographed over 1.1 kg of silica gel with a gradient of ethyl acetate in toluene of 10 to 15% to give 12.2 g of product, $R_f$(10% methanol/dichloromethane)≃0.84. Recrystallization from ethanol affords 10.2 g (50%) of product, as off-white crystals; mp 128°–131° C.

Example M

N-[2-(Diethylamino)ethyl]-4-(2-propynylamino)benzamide

To a refluxing solution of 4-aminobenzoic acid, 5 g (0.036 mol), and triethylamine, 11.1 g (0.11 mol), in diethyl ether is added dropwise thionyl chloride, 5.14 g (0.043 mol). After one hour, N,N-diethylethylenediamine, 6.28 g (0.054 mol), is added and the reaction is refluxed for another eight hours or until thin layer chromatography (TLC) indicates amide formation is complete. The solution is cooled to room temperature and filtered. The filtrate is washed with water and the organic layer is separated, dried (sodium sulfate), and filtered. The filtrate is concentrated in vacuo and the residue is dissolved in toluene. To this solution is added an 80% by weight solution of propargyl bromide in toluene, 10.7 g (0.072 mol), and triethylamine, 7.27 g (0.072 mol). The reaction is refluxed for twenty-four hours. Aqueous workup gives a crude mixture of mono and dialkylated benzamides which are separated by chromatography over silica gel to give the desired product.

Example N 3-(Diethylamino)-1-[4-(2-propynylamino)phenyl]-1-propanone 3-(Diethylamino)-1-[4-fluorophenyl]-1-propanone (*Pharmazie*, 35, H.7 (1980)), 5 g (0.022 mol), is treated with a mixture of propargylamine, 2.47 g (0.045 mol), potassium carbonate, 3.09 g, and potassium fluoride, 1.3 g (0.022 mol), in dimethylsulfoxide between 50° and 100° C. until TLC shows formation of the aminated product is complete. The reaction is poured into water and the solid is collected. Chromatography of the crude material over silica gel affords the desired product.

Example O 4-(Diethylamino)-1-[4-(2-propynylamino)phenyl]-1-butanone

A solution of 4-aminobenzonitrile, 5 g (0.042 mol), triethylamine, 8.55 g (0.085 mol), and an 80% by weight solution of propargyl bromide in toluene, 12.6 g (0.085 mol), in toluene is refluxed overnight. The solution is cooled to room temperature and poured into water. The organic layer is separated, dried (sodium sulfate), filtered, and concentrated in vacuo. The residue is purified by chromatography over silica gel to give 4-(2-propynylamino)benzonitrile.

4-(2-Propynylamino)benzonitrile, 5 g (0.032 mol), in tetrahydrofuran is treated with an excess of the Grignard reagent which is prepared from fresh magnesium and 3-diethylaminopropyl chloride hydrochloride, according to the procedure of Sodet, *Comptes Rendus*, 254, pp. 3105–3107 (1962), to afford the desired product.

Example P

2-Amino-5-methyl-6-[[(3,4,5-trimethoxyphenyl)amino]-methyl]-4(3H)-quinazolinone

A suspension of 3 g (0.00812 mol) of 5-methyl-6-[[(3,4,5-trimethoxyphenyl)amino]methyl-2,4-quinazolinediamine (UK 1,345,502) in 550 ml of 1N sodium hydroxide, under nitrogen, is heated, under reflux, for eighteen hours. The suspension is filtered to remove a small amount of insoluble material which is discarded. The filtrate is cooled and filtered to give 2.7 g of material. Trituration in 250 ml of hot ethanol gives 1.79 g (58.7%) of the product as an off-white solid; mp 261°–262° C.

We claim:

1. A compound of the formula

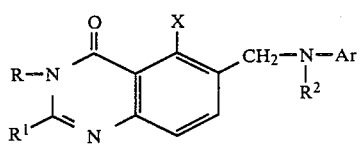

wherein R is hydrogen, an alkyl group of one to six carbon atoms, or

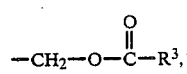

in which $R^3$ is an alkyl group of one to six carbon atoms; $R^1$ is hydrogen, an alkyl group of one to six carbon atoms, $-NR^4R^5$, in which $R^4$ and $R^5$ are each independently hydrogen or an alkyl group of one to six carbon atoms, or

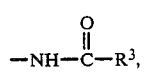

in which $R^3$ is as defined above; $R^2$ is an alkyl group of one to six carbon atoms, an alkenyl group of two to six carbon atoms, an alkynyl group of two to six carbon atoms, an alkynyl group substituted by $-NR^4R^5$, in which $R^4$ and $R^5$ are as defined above; X is hydrogen, an alkyl group of one to six carbon atoms, or halogen;

Ar is

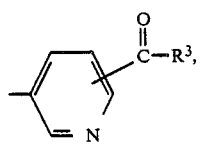

in which $R^3$ is as defined above, or

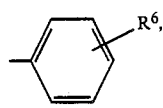

in which $R^6$ represents one or more substituents, the same or different, selected from the group consisting of hydrogen, hydroxy, alkoxy, halogen, nitro, cyano, $-OCF_3$, $-SO_2R^3$, in which $R^3$ is as defined above, $-SO_2NR^4R^5$, in which $R^4$ and $R^5$ are as defined above, $-NR^4R^5$, in which $R^4$ and $R^5$ are as defined above,

in which $R^3$ is as defined above,

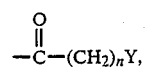

in which Y is halogen or $NR^4R^5$, in which $R^4$ and $R^5$ are as defined above and n is one to three,

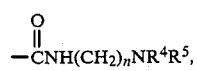

in which n, $R^4$, and $R^5$ are as defined above,

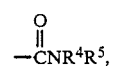

in which $R^4$ and $R^5$ are as defined above,

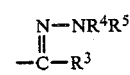

in which $R^3$, $R^4$, and $R^5$ are as defined above,

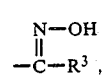

in which $R^3$ is as defined above,

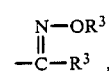

in which $R^3$ is as defined above, and

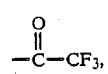

with the proviso that when $R^6$ is a single substituent $R^6$ is also selected from the group consisting of

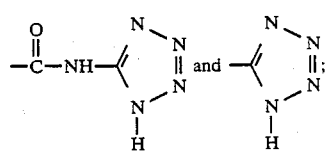

or a pharmaceutically acceptable acid or base addition salt thereof.

2. A compound according to claim 1, in which $R^2$ is an alkynyl group of two to six carbon atoms or a pharmaceutically acceptable acid or base addition salt thereof.

3. A compound according to claim 2, in which R is hydrogen, an alkyl group of one to three carbon atoms, or

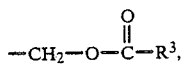

in which R³ is an alkyl group of one to six carbon atoms; R¹ is hydrogen, NH₂, or

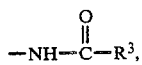

in which R³ is as defined above; X is hydrogen, an alkyl group of one to three carbon atoms, or halogen;
Ar is

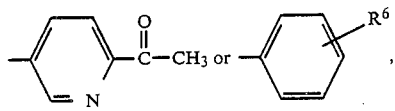

in which R⁶ represents one or more substitutents, the same or different, selected from the group consisting of hydrogen, methoxy, fluoro, nitro, cyano, —OCF₃, —SO₂N(CH₃)₂,

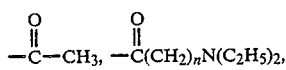

in which n is two to three,

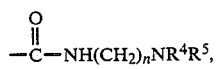

in which n, R⁴, and R⁵ are as defined above,

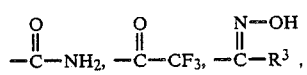

in which R³ is as defined above,

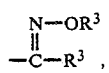

in which R³ is as defined above, and

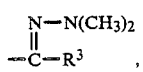

in which R³ is as defined above, with the proviso that when R⁶ is a single substitutent R⁶ is also

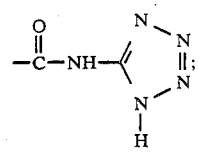

or a pharmaceutically acceptable acid or base addition salt thereof.

4. A compound according to claim 2, in which Ar is

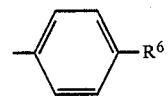

or a pharmaceutically acceptable acid or base addition salt thereof.

5. A compound according to claim 3, and being 6-[[2-propynyl-(3,4,5-trimethoxyphenyl)amino]methyl]-4-(3H)-quinazolinone.

6. A compound according to claim 3, and being 6-[[(3,4-dichlorophenyl)-2-propynylamino]methyl]-4(3H)-quinazolinone.

7. A compound according to claim 4, and being 6-[[(4-acetylphenyl)-2-propynylamino]methyl]-4-(3H)-quinazolinone.

8. A compound according to claim 3, and being 6-[[(2-acetyl-5-pyridinyl)-2-propynylamino]methyl]-4(3H)-quinazolinone.

9. A compound according to claim 4, and being 6-[[(4-acetylphenyl)-2-propynylamino]methyl]-2-amino-4(3H)-quinazolinone.

10. A compound according to claim 3, and being 2-amino-6-[[(3,4-dichlorophenyl)-2-propynylamino]methyl]-4(3H)-quinazolinone.

11. A compound according to claim 3, and being 2-amino-6-[[2-propynyl(3,4,5-trimethoxyphenyl)amino]methyl]-4(3H)-quinazolinone.

12. A compound according to claim 4, and being 2-amino-6-[[(4-nitrophenyl)-2-propynylamino]methyl]-4(3H)-quinazolinone.

13. A compound according to claim 4, and being 4-[[(2-amino-3,4-dihydro-4-oxo-6-quinazolinyl)methyl]-2-propynylamino]-N,N-dimethylbenzenesulfonamide.

14. A compound according to claim 4, and being 2-amino-6-[[2-propynyl[4-(trifluoroacetyl)phenyl]amino]methyl]-4(3H)-quinazolinone.

15. A compound according to claim 3, and being 2-amino-5-methyl-6-[[2-propynyl(3,4,5-trimethoxyphenyl)amino]methyl]-4(3H)-quinazolinone.

16. A method of inhibiting thymidylate synthase comprising administering to a host suffering therefrom a therapeutic effective amount of a compound according to claim 1 in unit dosage form.

17. A pharmaceutical composition adapted for administration as an inhibitor of thymidylate synthase comprising a therapeutic effective amount of a compound according to claim 1 in admixture with a pharmaceutically acceptable excipient, diluent, or carrier.

* * * * *